United States Patent [19]
Monticelli et al.

[11] Patent Number: 5,095,919
[45] Date of Patent: Mar. 17, 1992

[54] ARCUATE ELEMENT AND EXTERNAL FIXATION DEVICE

[75] Inventors: Georgio Monticelli; Renato Spinelli, both of Rome, Italy; Marcel Wagenknecht, Le Lignon, Switzerland

[73] Assignee: Jaquet Orthopedie S.A., Geneva, Switzerland

[21] Appl. No.: 253,155

[22] Filed: Oct. 4, 1988

Related U.S. Application Data

[63] Continuation of Ser. No. 821,671, Jan. 23, 1986, Pat. No. 4,784,125.

[30] Foreign Application Priority Data

Jan. 24, 1985 [CH] Switzerland .................. 309/85-4

[51] Int. Cl.⁵ .............................................. A61F 5/04
[52] U.S. Cl. ................................... 606/56; 606/57
[58] Field of Search ........................... 128/927, 922 Y

[56] References Cited

U.S. PATENT DOCUMENTS 2,055,024  9/1936  Bittner, Jr. ...................... 128/922
4,006,740  2/1977  Volkov et al. ................... 128/922

FOREIGN PATENT DOCUMENTS 3305597  8/1984  Fed. Rep. of Germany ...... 128/922

Primary Examiner—Richard J. Apley
Assistant Examiner—David J. Isabella
Attorney, Agent, or Firm—Peter C. Richardson; Lawrence C. Akers; Elizabeth O. Slade

[57] ABSTRACT

An arcuate cradle element for use in an external fixation device is generally in the shape of a partial or full circular toroid whose transverse cross-section comprises two opposed and symmetrical polygonal portions, joined by a web serving to connect and space apart the polygons. The polygonal portions are preferably triangular portions. Two of the arcuate cradle elements of unequal length may be combined to form a full circle.

8 Claims, 4 Drawing Sheets

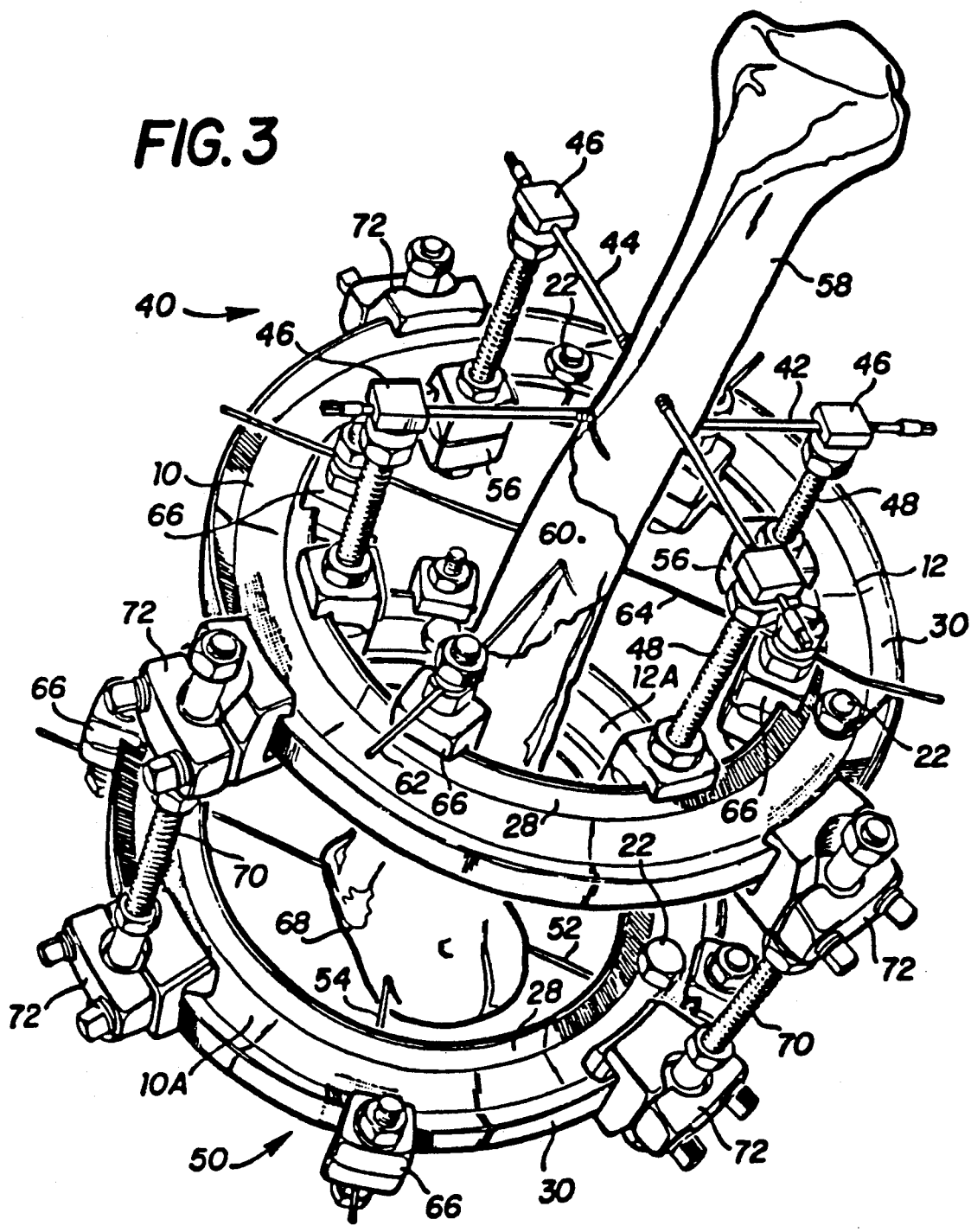

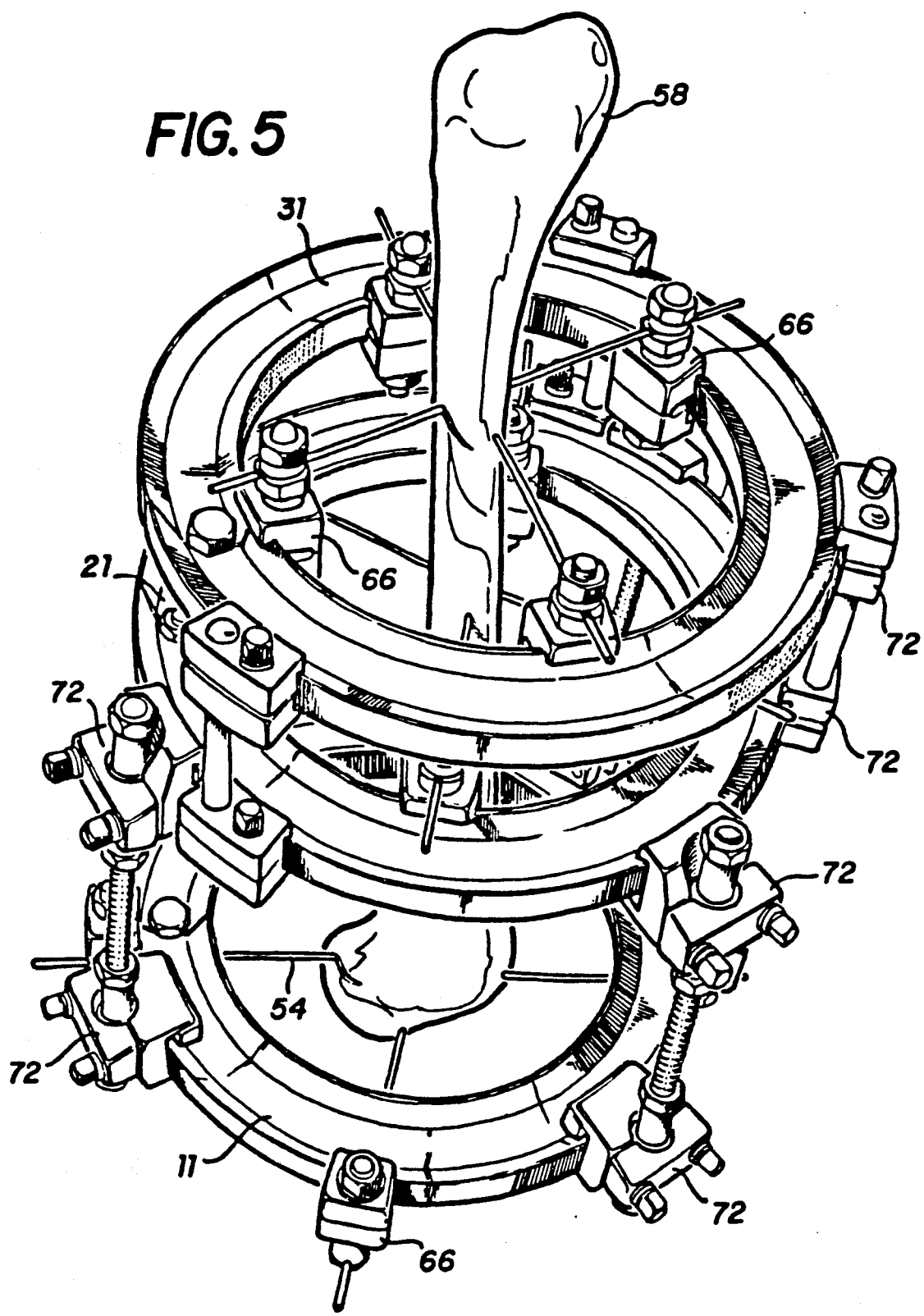

ARCUATE ELEMENT AND EXTERNAL FIXATION DEVICE

This is a continuation of application Ser. No. 821,671, filed on Jan. 23, 1986, now U.S. Pat. No. 4,784,125.

BACKGROUND OF THE INVENTION

The present invention relates to an arcuate cradle element intended for use in osteosynthesis and osteoplasty. It relates additionally to an external fixation means in which the arcuate element is incorporated in use.

External fixation is a classical practice in surgery, dating back a century. Its application has long been limited to complicated fractures in traumatology and later in orthopedics, namely in secondary treatments of fractures, infections, delayed consolidation, pseudarthrosis, faulty reduction, etc. External fixation is addressed specifically to the long bones, such as the femur, the tibia, the humerus, the radias and the ulna, particularly those of the leg.

External fixation means for osteosynthesis admit of two kinds of bone fixation:

Transfixing, where the pins pass all the way through the bone; and

Non-transfixing, where the pins enter into the bone but do not pass through it.

The transfixing kind of fixation, most commonly used on the leg, is more rigid than the non-transfixing kind. On either side of the leg are mounted two bars or frames, upon which are fixed two sets of pins placed on either side of the fracture. The two frames, or two bars, are connected by as stable a framework as possible, which may comprise sliding bars or rods whose length may be increased or decreased, thus effecting an extension or a compression respectively.

Such an external fixation system is disclosed in U.S. Pat. No. 4,365,624, which is incorporated herein by reference in its entirety. The arcuate element described in said patent has a polygonal, preferably triangular, cross-section. Such a section permits very quick assembly and disassembly and firm attachment of jaw brackets serving to hold the pins and the assembly rods.

SUMMARY OF THE INVENTION

The present inventors have developed a new system of external fixation means extending the use of such means to the pelvis, the clavicle, joints such as the knee, elbow, shoulder and great toe, for treatment of the cervical and lumbar vertebrae, etc.

It is an object of the present invention to enlarge the possibilities of application of the system disclosed in the aforesaid U.S. Pat. No. 4,365,624. In particular, it is an object to provide multiple and extended possibilities for assembly of the rods, pins and other connecting parts and members on the arcuate element intended to encircle the bone partially or completely.

These and other objects are accomplished with the arcuate cradle element according to the present invention, which has a generally toroidal shape, the transverse cross-section of which comprises two polygonal portions joined by a connecting and spacing web. An external fixation means according to the invention, comprising two sets of at least one pin or wire each, each holding a fragment of bone, with the two sets being connected by assembly rods, is characterized by comprising at least one arcuate cradle element as defined above, namely having a generally toroidal shape, the transverse cross-section of which comprises two polygonal portions joined by a connecting and spacing web.

The assembly and/or support parts ordinarily comprise jaws having internal recesses arranged to fit at least a portion of the perimeter of the arcuate element, so that they may be tightened and locked on the element with no possibility of rotation about it, and each assembly and/or support part may be provided with a hole into which the pin, rod or wire is inserted.

However, since the arcuate element comprises two polygonal portions, as a general rule in one horizontal plane of the toroid of the element, one polygon being on the outside and the other on the inside of the toroid, the assembly parts can be fixed on the inside and on the outside of the element, even on the same radius.

The hole in each support or assembly part may be fitted with a bushing or sleeve arranged to adapt the diameter of the wires and pins to that of the hole.

The hole may be drilled so that its centerline is radial to the arcuate element when the part is fixed thereon, or so that its centerline is perpendicular to the plane of the element when the part is so fixed.

The assembly part may have a portion pivoting around a tightening screw relative to the part as a whole, the pivoting portion including the hole, which piloting portion may take the forms of a flange having a hole and a slot.

According to a preferred embodiment, additional pins intended to hold additional bone fragments are fixed on the arcuate element by suitable means arranged to position the additional fragment laterally in relation to the element.

The two polygonal portions of the element cross-section may or may not be alike. They may be located in the same horizontal plane, as is preferred, or offset vertically from each other. The two polygonal portions are normally alike, so that the same assembly parts can be used with both. Preferably, the complete transverse cross-section is composed of two triangular portions and a rectangular connecting and spacing web, the triangles being substantially isosceles with their vertices pointing towards each other and merged with the connecting web.

The arcuate cradle element may form a portion of a circle, for example a quadrant, a semicircle or three quadrants, or else a complete circle. An embodiment is provided in which the arcuate element forms two-thirds to about three-quarters of a circle, so that a circle can be completed with another part having the same cross-section as the first and likewise capable of serving as an arcuate cradle element.

The arcuate element and fixation means according to the invention possess the advantages set forth in said U.S. Pat. No. 4,365,624. Furthermore, the new arcuate element lends itself to a closer assembly of the support and assembly parts of the rods and pins. A greater rigidity of the arcuate element has likewise been found, which is of course crucial to the success of operations of bone compression or extension.

DETAILED DESCRIPTION OF THE INVENTION

In the description to follow, any feature described and any combination of features meaningful in the art may constitute an invention or have inventive aspects.

The drawings show some practical embodiments by way of example.

In the drawings:

FIG. 3 is a perspective view of a fixation means of the invention mounted around a bone;

FIG. 5 illustrates the use of three arcuate elements forming full circles.

Figure 1:
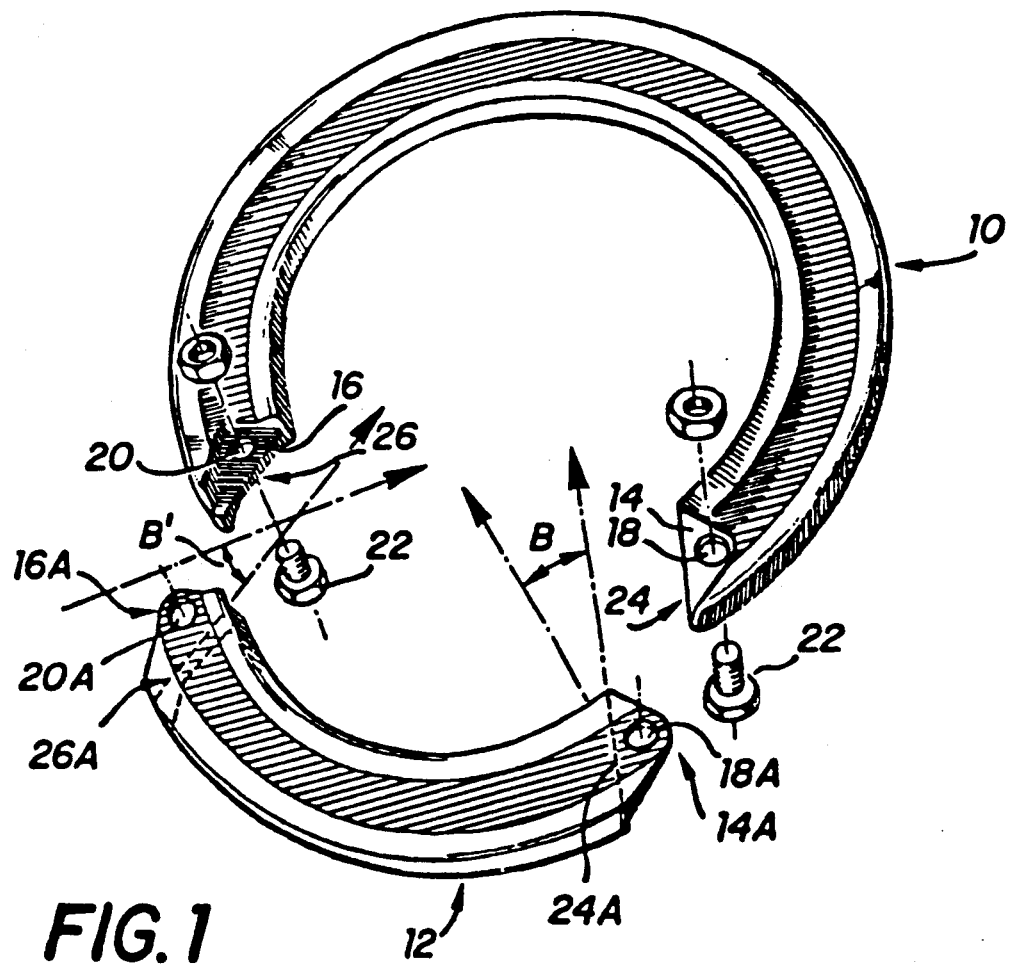
FIG. 1 is a perspective view of two arcuate cradle elements of the invention.

The larger arcuate cradle element 10 (see FIG. 1) occupies approximately three-quarters (or alternatively about two-thirds) of a circle, while the part 12 is of a suitable arc length to complete the circle.

Parts 10 and 12 are arranged at their circular ends to be capable of being fixed to each other, thus forming the complete circle. For that purpose, the terminal portions 14, 16 of part 10 are cut horizontally at the middle of the cross-section of the part, and the corresponding terminal portions 14A and 16A respectively of part 12 are cut out in complementary fashion. The pairs of holes 18, 18A and 20, 20A serve to connect parts 10 and 12 by means of bolts 22. However, the holes 18, 18A and 20, 20A serve an alternative purpose to be described later.

The vertical faces 24, 24A and 26, 26A, of the partially cut ends of the two parts form angles B, B' with the plane of the perpendicular at the same place. The angles B, B' are preferably equal. The planes of the faces 24A and 26A may be parallel of form an angle between them; the provision of the angles B, B' greatly facilitates assembly and disassembly of part 12 with or from part 10. If the aforementioned angle (no reference) between said planes of the vertical faces is an acute angle with its vertex towards the center of the circle formed by the arcuate elements, the solidity of the assembly is increased. The firmness and rigidity of the connection between the two elements 10 and 12 are likewise increased because the cuts 14, 14A and 16, 16A are not straight but bowed (see FIG. 1).

Figure 2:
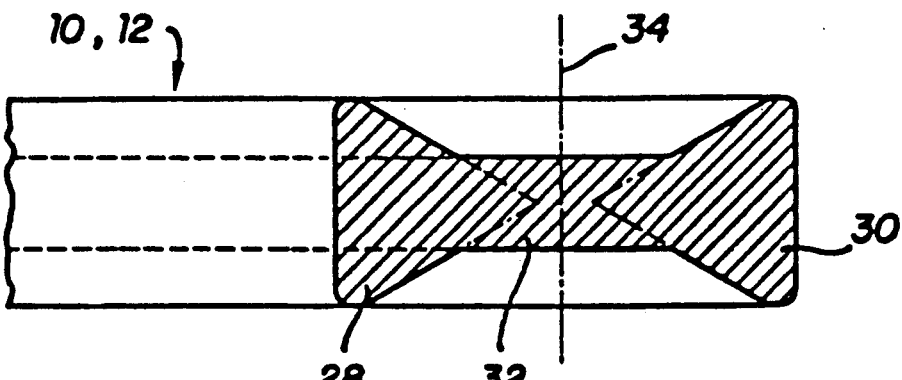
FIG. 2 is a vertical section of the toroid forming the arcuate element, exhibiting its transverse cross-section.

The toroid formed by the contour of the arcuate elements is represented in vertical section in FIG. 2. The cross section of the element 10 or 12 of the invention consists of two portions in the shape of congruent isosceles triangles 28 and 30, whose vertices, merged with the connecting and spacing web (center, crosspiece) 32 of rectangular shape, face each other. Hence the complete cross-section is symmetrical with respect to the vertical cylindrical surface 34.

The external fixation means shown in FIG. 3 will now be described in detail. For parts, members and features not described, and for general information as well, reference is made to the description of said U.S. Pat. No. 4,365,624.

The external fixation means for skeletal immobilization shown in FIG. 3 is applied as follows. The two sets 40 and 50, of pins 42, 44 and 52, 54, respectively, are positioned with the aid of a gauge or guide and a brace not shown. The pins of set 40 may be located and secured without difficulty between the jaws of the fixation parts 46 of the pins or rods 42, 44. The fixation parts 46 are screwed to the top of the threaded rods 48 mounted in the clamps 56; these clamps 56 are secured to the arcuate elements 10, 12, joined by means of bolts 22, at the inner triangular portion 28 of the element.

The transfixing pins 42, 44 hold the top bone fragment 58 in place. An intermediate fragment 60 is retained by transfixing wires 62 and 64 held under tension directly, with no rod, by means of clamps 66 (the construction of which is described in U.S. Pat. No. 4,365,624) likewise secured on the inner section 28 of the upper element.

A third bone fragment 68 is held in place by transfixing wires 52 and 54 directly supported by clamps 66 secured on the outer section 30 of the lower element 10A, 12A.

The two arcuate elements 10, 12 and 10A, 12A are joined at a distance, with absolute rigidity and firmness, by three or four threaded rods 70 fixed to the outer triangular sections 30 of the two arcuate elements 10, 12'; 10A, 12A by clamps 72; these clamps 72 are so arranged as to permit an axial adjustment, and hence a compression or extension of the bone.

Figure 4:
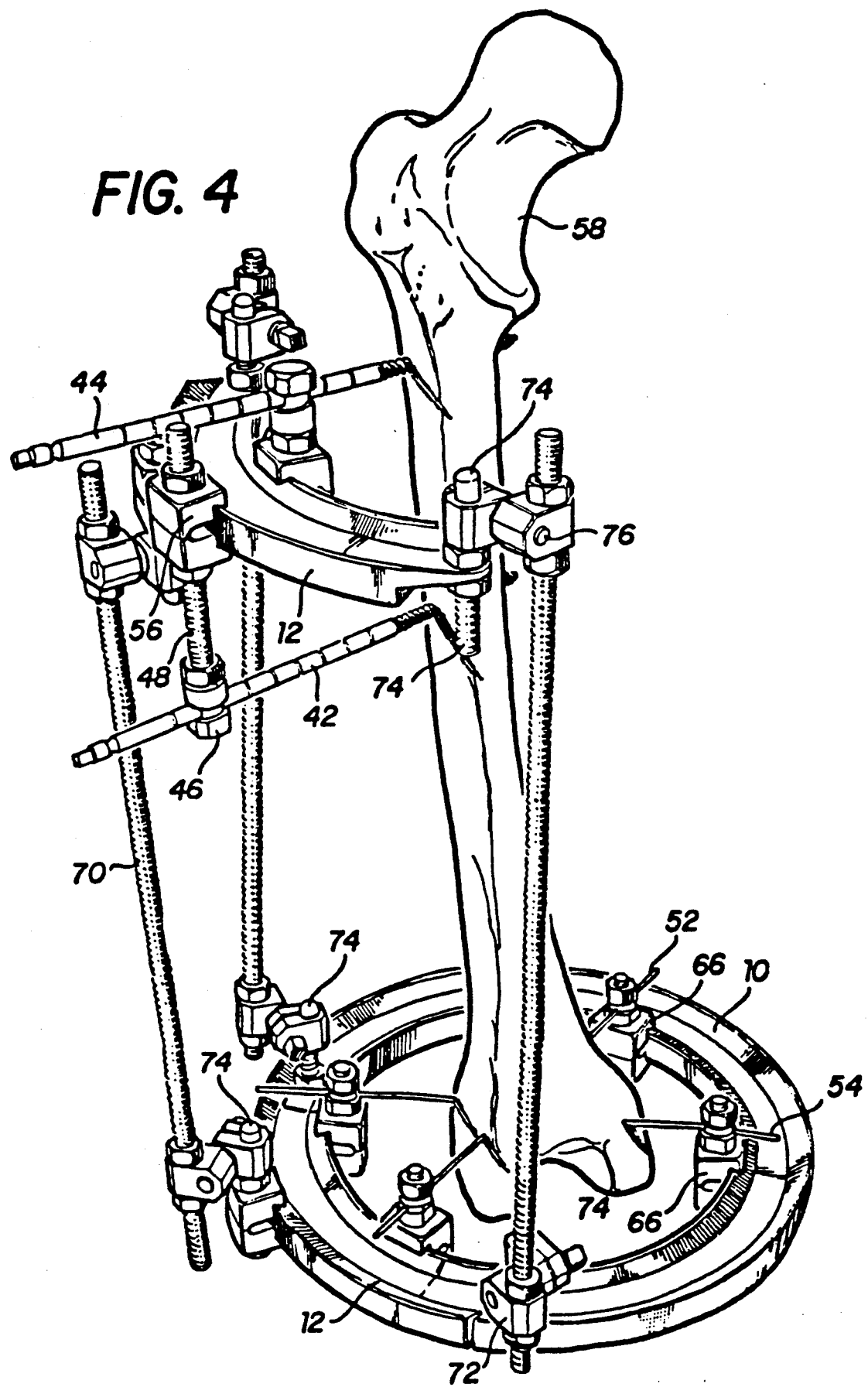
FIG. 4 illustrates the application of an arcuate element forming a partial circle.

FIG. 4 illustrates the use of a partial arcuate element 12, with no complete circle being formed. The holes 18A, 20A (see FIG. 1) here serve to accept bar bolts 74 for the assembly of connecting parts 76. The other members correspond to those of FIGS. 1 to 3.

FIG. 5 represents a fixation means according to the invention comprising three full-circle arcuate elements 11, 21, 31. This fixation means is used for osteosynthesis of multiple complex fractures. The other members and parts used to apply this fixation means have already been described. Specially shown in FIG. 5 are the desirability and particular advantages of the arcuate element with double polygonal clamping cross-section according to the invention, permitting parts to be secured to the outer and the inner peripheries of the element. It is also to be noted that the several clamps (56, 66, 72) may be used on either of these two portions indifferently, owing to the identical and symmetrical cross-sectional portions 28 and 30.

We claim:

1. An arcuate assembly for use in osteosynthesis having two parts, each of said two parts being an arcuate element having generally a shape of a part of a toroid and forming a portion of a circle and having a transverse cross-section comprising two polygonal portions joined by a connecting and spacing web, with said two parts having circular arc lengths such that they together form a full circle, and with the ends of said two parts being cut both parallel to the plane of said full circle and being cut perpendicularly to the plane of said full circle by perpendicular cuts so that said two parts form interengaging planar surfaces which fit into one another to form said full circle, with the planes of said perpendicular cuts in said ends forming acute angles B and B' with the respective planes passing through said cuts perpendicular to the plane of and through the center of said full circle.

2. A device according to claim 1, wherein said ends of said two parts are cut in a manner such that a portion of one of said interengaging planar surfaces lies only on top of the other of said interengaging planar surfaces and wherein said interengaging surfaces interengage also along a bowed cut.

3. A device according to claim 2, wherein said two parts are unequal in size.

4. A device according to claim 3, wherein said acute angles B and B' are equal.

5. A device according to claim 4, wherein said two polygonal portions are isosceles triangular portions having their apices directed toward each other.

6. A device according to claim 5, wherein said isosceles triangular portions are identical isosceles triangular portions.

7. A device according to claim 6, wherein the centers of said two polygonal portions lie in the same horizontal plane of the toroid.

8. A device according to claim 1, wherein said perpendicular cuts lie in non-parallel planes.

* * * * *